United States Patent [19]

Bonadeo

[11] Patent Number: 4,567,203

[45] Date of Patent: Jan. 28, 1986

[54] COSMETICS INTEGRATED WITH EPICUTANEOUS SEBUM AND SEBUM-LIKE COMPOSITIONS

[76] Inventor: Igino Bonadeo, Via Cornalia 32, Milan, Italy

[21] Appl. No.: 51,036

[22] Filed: Jun. 22, 1979

Related U.S. Application Data

[63] Continuation-in-part of Ser. No. 843,678, Oct. 19, 1977, abandoned.

[51] Int. Cl.$^4$ ............................................. A61K 47/00
[52] U.S. Cl. .................................... 514/844; 514/846
[58] Field of Search ....................... 424/365; 514/844

[56] References Cited

PUBLICATIONS

Formulary of Typical Pharmaceutical Formulations for Topical Application, 5/1961, pp. 3 to 30, 31, 36, 46 & 47.
Atlas Formulary, 3/1958, pp. 12 to 22, 24, 25, 27, 28 & 29.
Atlas Cosm. Bulletin, 3/1958, pp. 1 & 2.
Catalog of Atlas Products, 7/1964, pp. 7 to 13.
Atlas Guide, 3/1958, pp. 4–20.
Kirk–Othmer, "Encyclopedia of Chemical Technology", Second Edition, vol. 8, John–Wiley & Sons, pp. 127–137, (1965).

*Primary Examiner*—Dale R. Ore
*Attorney, Agent, or Firm*—Fitzpatrick, Cella, Harper & Scinto

[57] ABSTRACT

A sebum-like cosmetic composition having a required value of emulsification equal to or substantially equal to that for the sebaceous film of the human body zone to which said cosmetic unit is applied is disclosed.

10 Claims, 1 Drawing Figure

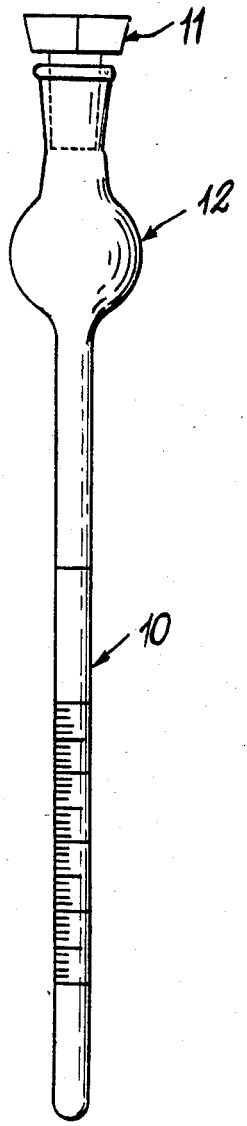

COSMETICS INTEGRATED WITH EPICUTANEOUS SEBUM AND SEBUM-LIKE COMPOSITIONS

RELATED APPLICATIONS

This application is a continuation-in-part of my copending application Ser. No. 843,678, filed Oct. 19, 1977, now abandoned.

BACKGROUND OF THE INVENTION

This invention relates to cosmetic compositions having characteristics consistent with those of the sebaceous skin or hair film.

It is known that sebum secretion is related to the protective functions of the skin since, by impregnating the horny layer of the skin, it normalizes heat conductivity and interferes with the drying effect of the atmosphere on the skin.

Therefore, in the cosmetic art, attempts have always been directed both to complying with integrity of epicutaneous sebaceous film, and to restoring said film with units having the same characteristics as sebum. However, these purposes have never been effectively attained because, on formulating such units, only the chemical features of normal sebaceous secretion have been taken into account.

Cosmetic compositions of the kind set forth above fall within two classes:

(a) Sebum-like units having the same characteristics as sebaceous film and exhibiting compensating and complementary effects of said film; and (b) Sebotropic units, suitable to cleanse skin and hair, while restoring the sebaceous film required and sufficient for cutaneous physiological defense.

Sebum-like cosmetics hitherto commercially available were always formulated to imitate the chemical characteristics of sebaceous secretion, without taking into account the well defined physical characteristics of sebum. When applying said products, to which it was intended to assign compensating and complementary effects of sebaceous film, the presence of said film on the skin and its incidence on topical forms was not kept in mind. As a matter of fact, said sebum-like cosmetics so far commercially available act upon the skin and its horny-like glandular formations by apposition, that is to say by being superimposed on the treatment zone where, to achieve the relevant cosmetological activity thereof, they break up the epicutaneous sebaceous film.

In hitherto commercially available sebotropic units, or units having a washing action for cleansing the skin and its productions, particularly hair i.e., soaps and shampoos, the cleansing phenomenon could never be controlled to remove excess sebum associated with dirt, complying with the sebaceous film required and sufficient for cutaneous physiological defense.

At present, physiology and biochemistry recognize that epicutaneous sebaceous film, in its natural function between the human body and surrounding environment, is the most efficient and immediate cutaneous protective system. Furthermore, pathology grants that the destruction and disorderly overthrow of its structure is equivalent to exposing the individual to unfailing disfunctional upsettings such as, for example, scurf resulting from capillary cleansing agents, skin reddening and allergic events due to awkward transcutaneous penetration of chemical agents.

SUMMARY OF THE INVENTION

All of the above deficiencies are overcome when considering, in addition to chemical characteristics, also quite defined physical characteristics of sebum, which have not been so far sufficiently emphasized. The primary of these physical characteristics is the "required value for emulsification" ($HLB_r$) of sebum. This value is of basic importance for emulsion of cutaneous sebum, which emulsion allows compensation and complements said sebaceous film or cleaning of the skin or hair while complying with the integrity of said film.

The required value of emulsification for human sebum substantially varies according to the cutaneous zone. However, for a proper statistically significant extensive range, comprising men and women in the age of 15 to 60, the average values are as follows:

(1) Face sebum, $HLB_r = 10.4$–$10.7$
(2) Hair sebum, $HLB_r = 12.4$–$12.8$

These values, that have been accurately determined by a method and measuring apparatus to be described hereinafter, allow formulation of cosmetic preparations having particular characteristics. Moreover, the knowledge of these values enables one to prepare an emulsifying unit having the desired "emulsification value" (HLB).

The use of this physical characteristic of epicutaneous sebum permits:

(1) Formulation of sebotropical cosmetics, that is, emulsifying units having an emulsification value (HLB) equal to the required value of emulsification ($HLB_r$) of sebum.

These cosmetics are suitable to provide a particular cleansing of the skin, characterized in that dirt is removed by emulsification, while cosmetic cleansing agents operate by dispersion or abstergency, and said modality involves the compliance with integrity of sebaceous film penetrating the horny layer of the skin, essential for physiological integrity.

(2) Formulation of sebum-like cosmetics, that is units having the same required value of emulsification ($HLB_r$) as sebum. Both natural sebaceous film and artificial sebum-like units are included as distinguishing ingredients in these cosmetics. In any case, the normal sebaceous film is of essential importance, both as to cosmetic structure and fulfilment of cosmetological goals thereof.

The compositions comprise mixtures of fatty acids such as isostearic acid and palmitic acid; fatty esters such as acetylated lanolic alcohols, lanolin isoesters and lanolin oil; fatty hydrocarbons such as nor-and isohydrocarbons including petrolatum oil; and fatty alcohols such as lanolin alcohol. The compositions may also include emulsifying agents such as polyoxyethylen-20-sorbitan-monostearate, polyoxyethylen-4-sorbitan-monostearate and polyoxyethylen-20-sorbitan-monopalminate; and cosmetic wax such as bleached beeswax. Those skilled in the art will appreciate that other specific components falling within the general categories set forth above may be utilized in the present invention insofar as such components are non-toxic and, in combination with other constituents give a final composition having the required value of emulsification ($HLB_r$) or emulsification value (HLB) as the case may be. In this regard appropriate fatty acids have a $HLB_r$ of between 12.7 and 17; appropriate fatty esters have a $HLB_r$ of between 8.2 and 12.7; appropriate fatty hydrocarbons have a $HLB_r$ of between 8.2 and 12; appropriate fatty alcohols have a $HLB_r$ of between 9.4 and 12.7. Where a cosmetic wax is included in the composition an appropriate wax should have a $HLB_r$ of between 10 and 17. When the composition includes an emulsifying agent, an appropriate agent has a HLB of between 9 and 19. Moreover, the compositions of the invention may also include other constituents such as scents or the like as is appropriate in the cosmetic art. In the present invention scented compositions should not exceed about 0.5% of the total weight of the composition.

DESCRIPTION OF THE INVENTION

The use of the required value of emulsification relating to human sebum within the above specified ranges can be carried out to provide a great deal of sebum-like compositions, or sebotropic cosmetic forms, as shown by the following examples forming specific embodiments of the invention for purposes of illustration.

EXAMPLE 1

| Fat sebum-like composition $HLB_r$ = 10.5 | |
| --- | --- |
| isostearic acid ($HLB_r$ = 13) | 12% |
| lanolin isoesters ($HLB_r$ = 11.5) | 30% |
| lanolin alcohols ($HLB_r$ = 10.5) | 28% |
| nor-and isohydrocarbons ($HLB_r$ = 8.5) | 30% |

EXAMPLE 2

| Sebum-like emulsion | |
| --- | --- |
| sebum-like composition as in Example 1 | 30.00% |
| polyoxyethylen-20-sorbitan-monostearate (HLB = 14.9) | 1.70% |
| polyoxyethylen-4-sorbitan-monostearate (HLB = 9.6) | 8.30% |
| butylhydroxyanisole | 0.02% |
| methyl-p-oxybenzoate | 0.23% |
| scented composition | 0.25% |
| demineralized water | 59.50% |

EXAMPLE 3

| Sebum-like hydrophile unguent, $HLB_r$ = 10.7 | |
| --- | --- |
| palmitic acid ($HLB_r$ = 16) | 7.75% |
| Pitrolatum oil ($HLB_r$ = 11) | 12.00% |
| acetylated lanolic alcohols ($HLB_r$ = 8.5) | 26.75% |
| lanolin oil ($HLB_r$ = 11.5) | 30.00% |
| bleached beeswax ($HLB_r$ = 10.3) | 18.00% |
| polyoxyethylen-4-sorbitan-monostearate (HLB =9.6) | 3.98% |
| polyoxyethylen-20-sorbitan-monopalmitate (HLB = 15) | 1.02% |
| butylhydroxyanisole | 0.02% |
| scented composition | 0.48% |

EXAMPLE 4

| Sebotropic capillary cleansing agent, HLB = 12.5 | |
| --- | --- |
| polyoxyethylen-0,5-lauryl-sodium sulphate (HLB = 18) | 8.43% |
| polyoxyethylen-4-lauryl-ether (HLB = 9.7) | 16.57% |
| methyl-p-oxybenzoate | 0.20% |
| ethylenglycol-monophenyl-ether | 0.50% |
| scented composition | 0.30% |
| demineralized water | 74.00% |

The method for accurately determining the required value of emulsification of sebum is extremely important.

In the past, this method used a 50 ml thermostable indexed cylinder made of glass and provided with a standardized plug therein precisely metering 10 ml fat product, 20 ml pure dioxane and 10 ml distilled water. The mixture was then stirred to provide a homogeneous emulsion and then allowed to rest until separation of two layers. The supernatant showed an increase in volume ($C_o$) relative to the fat body or product and an increase in volume ($C_a$) in the underlying layer with respect to water. The ratio of distributed dioxane establishes the "distribution coefficient" ($K_d$), that is:

$$K_d = \frac{C_o}{C_a}$$

From said distribution coefficient, the required value of emulsification for the fat body or product could then be calculated.

When using this method applied to sebum, the major problem is given by the required amount of sebum for measurements, since at a pure state sebum can be hardly extracted, particularly at substantial amounts of a few ml.

With the present method, and by using the novel metering apparatus shown in FIG. 1, the distribution coefficient can be obtained and the required value of emulsification for sebum can be calculated, using minimal amounts of said material. This is achieved by using as a carrier for sebum in the measuring process, another fat material, in this case silicone oil, the distribution coefficient of which is already known. The use of this carrier, forming the major portion of the fat layer, provides for requirements of minimal amounts of sebum in the measuring process for the required value of emulsification.

The measuring apparatus shown in FIG. 1 comprises: a distribution tube 10 of thermostable glass, closed at one end, calibrated and fitted with a plug 11, having a capacity of 4 ml (tolerance 0.010), with emulsifying bubble 12, indexed between 0–4 ml, with divisions of 1/20 from 1 to 3 ml.

The required values for emulsification of sebum were found by measuring the variation in the distribution coefficient of dioxane, expressed as value $K_d$, on silicone oil ($d_4 \cdot 20° = 0.970-0.975$; viscosity, cps=365–375; $K_d=0.07$) from sebum drawn on the face, hair and other sound cutaneous parts of the human body of voluntary individuals.

In the measuring process, use is made of three microsyringes having an interchangeable needle, of which one with a capacity of 100 μl and the other two (without any needle) with a capacity of 1000 μl, and a calibrated pipette with a capacity of 2 ml, tolerance 0.010.

Measurements were carried out by operating as follows: 900 μl silicone oil were drawn by a microsyringe having a capacity of 1000 μl and added in said distribution cylinder to 100 μl sebum drawn by means of a suitable microsyringe; then the fat bodies or materials were added with 2 ml dioxane ($d_4 \cdot 20° = 1.034$) precisely metered by said pipette and then with 1000 μl distilled water metered by suitable microsyringe. The tube was then plugged and the mixture in the bubble and tube cylinder was thoroughly stirred. The mixture was then allowed to rest to separation of the emulsion resulting from stirring, separation into two layers, i.e. a supernant oily layer ($C_o$) and an underlying aqueous layer ($C_a$).

The distribution coefficient $K_{d(9:1)}$ of dioxane between the fat mixture (comprising silicone oil and sebum in a ratio of 9:1) and the aqueous layer, is given by:

$$K_{d(9:1)} = \frac{C_o}{C_a}$$

Having calculated the coefficient $K_{d(9:1)}$ for the fat material, $K_d$ relative to sebum could then be experimentally obtained. By using the method of minimum scaled squares, and a computer for a calculation by a mathematic program, the valid equation for the calculation of values $K_d$ has the following form:

$$K_d = -4,3682462 + 146.03196x - 162.70075x^2 - 3788.5117x^3 + 25089.395x^4,$$

wherein $x = K_{d(9:1)}$ experimentally determined.

These values $K_d$ being known, the associated values $HLB_r$ are determined by applying the equation known in literature:

$$HLB_r = 5.75 + 6.6\, K_d$$

As it will be appreciated, the measuring step is carried out by using 1/100 of sebum that would have been required by using the prior art processes.

What is claimed is:

1. A cosmetic composition comprising a mixture of constituents selected from the group consisting of fatty acids, fatty esters, fatty hydrocarbons and fatty alcohols, said mixture being in a percent by weight ratio to obtain a required value of emulsification ($HLB_r$) of between 10.4 and 10.7 for a face treatment and of between 12.4 and 12.8 for a hair treatment and an emulsification value (HLB) of between 10.4 and 10.7 for emulsifying sebaceous face film and of between 12.4 and 12.8 for emulsifying sebaceous hair film wherein said fatty acids have a $HLB_r$ of between 12.7 and 17; said fatty esters have a $HLB_r$ of between 8.2 and 12.7, said fatty hydrocarbons have a $HLB_r$ of between 8.2 and 12; and said fatty alcohols have a $HLB_r$ of between 9.4 and 12.7.

2. A cosmetic composition according to claim 1, further comprising at least one emulsifying agent having a HLB of between 9.6 and 15.

3. A cosmetic composition according to claim 1, further comprising a cosmetic wax.

4. A cosmetic composition according to claim 1, further comprising a scented composition in an amount not exceeding about 0.5% of the total weight of the composition.

5. A cosmetic composition according to claim 1, wherein said fatty acid is selected from the group consisting of isosteric acid and palmitic acid.

6. A cosmetic composition according to claim 1, wherein said fatty ester is selected from the group consisting of acetylated lanolic alcohols, lanolin isoesters and lanolin oil.

7. A cosmetic composition according to claim 1, wherein said fatty hydrocarbon is selected from the group consisting of petrolatum oil, nor-and isohydrocarbons.

8. A cosmetic composition according to claim 1, wherein said fatty alcohol is lanolin alcohol.

9. A cosmetic composition according to claim 2, wherein said emulsifying agent is selected from the group consisting of polyoxyethylen-20-sorbitan-monostearate, polyoxyethylen-4-sorbitan-monostearate and polyoxyethylen-20-sorbitan-monopalminate.

10. A cosmetic composition according to claim 3, wherein said cosmetic wax is bleached beeswax.

* * * * *

UNITED STATES PATENT AND TRADEMARK OFFICE
CERTIFICATE OF CORRECTION

PATENT NO. : 4,567,203
DATED : January 28, 1986
INVENTOR(S) : Igino Bonadeo

It is certified that error appears in the above-identified patent and that said Letters Patent is hereby corrected as shown below:

Column 3, (Example 3), line 45, "Pitrolatum" should read -- Petrolatum --.

Signed and Sealed this

Eighth Day of July 1986

[SEAL]

Attest:

Attesting Officer

DONALD J. QUIGG

Commissioner of Patents and Trademarks